United States Patent [19]

Funk et al.

[11] Patent Number: 5,594,083
[45] Date of Patent: Jan. 14, 1997

[54] WATER-SWELLABLE HYDROPHILIC POLYMERS

[75] Inventors: Rüdiger Funk, Niederhausen; Fritz Engelhardt; Ulrich Riegel, both of Frankfurt am Main; Michael Wessling, Maintal, all of Germany

[73] Assignee: Cassella Aktiengesellschaft, Germany

[21] Appl. No.: 408,534

[22] Filed: Mar. 22, 1995

[30] Foreign Application Priority Data

Apr. 2, 1994 [DE] Germany ............... 44 11 536.9

[51] Int. Cl.$^6$ .............. C08F 20/58; C08F 4/36
[52] U.S. Cl. ............ 526/232.3; 526/200; 526/218.1; 526/277; 526/287; 526/288; 526/303.1; 526/304
[58] Field of Search .............. 526/232.3, 200, 526/304, 288

[56] References Cited

U.S. PATENT DOCUMENTS

| | | | |
|---|---|---|---|
| 4,777,230 | 10/1988 | Kamath | 526/86 |
| 5,039,754 | 8/1991 | Sanchez | 525/333.8 |
| 5,219,969 | 6/1993 | Uhl | 526/304 |
| 5,254,650 | 10/1993 | Fukumura | 526/232.3 |
| 5,258,465 | 11/1993 | Suyama | 525/263 |

FOREIGN PATENT DOCUMENTS

| | | |
|---|---|---|
| 0545126 | 6/1993 | European Pat. Off. |
| 4338867 | 6/1994 | Germany . |
| 93/19099 | 9/1993 | WIPO . |
| 93/24153 | 12/1993 | WIPO . |

*Primary Examiner*—Fred Zitomer
*Attorney, Agent, or Firm*—Connolly & Hutz

[57] ABSTRACT

Water-swellable hydrophilic polymers which contain polymers prepared by free radical (co)polymerization of one or more hydrophilic monomers of the formula I

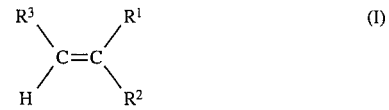

wherein $R^1$ is hydrogen, methyl or ethyl, $R^2$ is the group —COOR$^4$, the sulphonyl group, the phosphonyl group, the phosphonyl group esterified by ($C_1$–$C_4$)-alkanol or a group of the formula

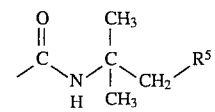

$R^3$ is hydrogen, methyl, ethyl or the carboxyl group, $R^4$ is hydrogen, amino or hydroxy-($C_1$–$C_4$)-alkyl and $R^5$ is the sulphonyl group, the phosphonyl group or the carboxyl group, or grafting (co)polymerization of one or more hydrophilic monomers of the formula I onto a grafting base, using a free radical initiator which forms three or more free radical sites per molecule.

19 Claims, No Drawings

WATER-SWELLABLE HYDROPHILIC POLYMERS

The present invention relates to water-swellable hydrophilic polymers which can be prepared by free radical polymerization using free radical initiators which form di- or poly-radicals.

Water-swellable hydrophilic polymers, in particular crosslinked polymers and copolymers based on acrylic or methacrylic acid, acrylamidopropanesulphonic acid copolymers or graft polymers on starch or polyalkylene oxides, have been known for a long time and are described, for example, in U.S. Pat. Nos. 4,931,497, 5,011,892, 5,041,496, 3,926,891 and the literature references cited therein.

They can absorb several times their weight of water or aqueous liquids, such as urine or blood, and are therefore employed as absorbents, in particular in hygiene articles such as nappies for babies and incontinence pants for adults, and also tampons and the like.

Such water-swellable hydrophilic polymers are as a rule prepared by free radical polymerization in an aqueous solution which contains the monomers and, if appropriate, grafting base and crosslinking agent. The polymerization can be initiated by high-energy radiation and/or chemically. Chemical initiators which are employed here are, for example, peroxide compounds, such as peroxodisulphates, hydrogen peroxide, benzoyl peroxide, tert.-butyl hydroperoxide or tert.-butyl perpivalate, azo initiators, such as 2,2'-azobis(isobutyronitrile) (AIBN) or 2,2'-azobis(2-amidinopropane) dihydrochloride, or redox systems, such as, for example sodium peroxodisulphate/sodium pyrosulphite or hydrogen peroxide/hydroxylamine chloride. Benzoin, benzil and derivatives thereof or acetophenone derivatives can also be used as photo-initiators. All these initiators have the common feature that they form mono-radicals which trigger off the polymerization.

However, the products prepared in this manner have various network defects which are due to unwanted secondary reactions during the polymerization and which adversely influence the properties of the products. For example, oligomers are formed which are not incorporated into the polymeric network and therefore can be extracted from the swollen network and are thus inactive constituents. In addition, polymer chains which are bonded to the network on only one side are also inactive.

It has now been found that the network defects mentioned can be avoided or largely avoided if compounds which instead of forming only one free radical site per molecule, such as the compounds previously employed according to the prior art, form two or more free radical sites per molecule are employed as the free radical initiators.

The present invention thus relates to water-swellable hydrophilic polymers which can be prepared by free radical (co)polymerization of one or more hydrophilic monomers or graft (co)polymerization of one or more hydrophilic monomers onto a suitable grafting base, characterized in that a free radical initiator which forms two or more free radical sites per molecule is employed.

Suitable hydrophilic monomers are, for example, acids which are capable of polymerization, such as acrylic acid, methacrylic acid, caproic acid, vinylsulphonic acid, vinylphosphonic acid, maleic acid, including the anhydride thereof, fumaric acid, itaconic acid, 2-acrylamido-2-methylpropanesulphonic acid and their amides, hydroxyalkyl esters and esters and amides containing amino groups or ammonium groups. Water-soluble N-vinylamides or else diallyldimethylammonium chloride are furthermore suitable.

Preferred hydrophilic monomers are compounds of the general formula I

 (I)

wherein
$R^1$ is hydrogen, methyl or ethyl,
$R^2$ is the group —COOR$^4$, the sulphonyl group, the phosphonyl group, the phosphonyl group esterified by ($C_1$–$C_4$)-alkanol or a group of the formula

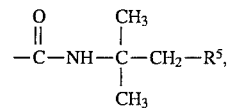

$R^3$ is hydrogen, methyl, ethyl or the carboxyl group,
$R^4$ is hydrogen, amino or hydroxy-($C_1$–$C_4$)-alkyl and
$R^5$ is the sulphonyl group, the phosphonyl group or the carboxyl group.

Particularly preferred hydrophilic monomers are acrylic acid and methyacrylic acid.

Suitable grafting bases can be of natural or synthetic origin. Examples are starch, cellulose or cellulose derivatives and other polysaccharides and oligosaccharides, polyalkylene oxides, in particular polyethylene oxides and polypropylene oxides, and hydrophilic polyesters.

Starch and polyethylene oxides and polypropylene oxides, in particular those described in U.S. Pat. Nos. 4,931,497, 5,011,892 and 5,041,496, are preferred. The content of these patents is also expressly a constituent of the present disclosure.

All compounds which form two or more free radical sites per molecule with or without the action of additional activators, such as light, radiation, heat, ultrasound, redox agents and the like, can in principle be employed as free radical initiators. This means that these free radical initiators can contain two, three or more groups which can form the radicals. The free radical sites can be formed here at the same time, but as a rule they are formed at different times, i.e. in succession. Compounds which contain at least two hydroperoxide units, peroxide units or azo units, for example, are suitable.

Compounds having two hydroperoxide units are, in particular, diisopropylbenzene dihydroperoxide (U.S. Pat. No. 2,715,646) and 2,5-dimethylhexane 2,5-dihydroperoxide. Suitable polyhydroperoxides can be obtained, for example, by anodic oxidation of polycarboxylic acids, in particular of polyacrylic acid and polymethacrylic acid, in the presence of oxygen (J. Pol. Sci. Volume XXXIV, pages 287 to 307 (1959)).

Peroxide units can be present, for example, as percarbonate or as perketal or perester units. Examples of such compounds are, in particular, dioxetane compounds and tert.-butyl peresters, such as, for example, methyl acrylate/tert.-butyl peracrylate copolymers (J. Pol. Sci. Volume XXXIV, page 301 (1959)). Polymeric peroxy-esters furthermore can be obtained by reaction of dicarboxylic acid dichlorides with bishydroperoxides (EP-A 461 767).

Suitable compounds having several peroxide or hydroperoxide units and syntheses thereof furthermore are described in "The Chemistry of Functional Groups, Peroxides", edited by S. Patai 1983, John Wiley & Sons Ltd., Chapter 13, by Ray Ceresa. The content of this publication is expressly a constituent of the present disclosure.

It is preferable to employ free radical initiators containing hydroperoxide or peroxide units together with reducing agents. Suitable reducing agents are, for example, $Fe^{2+}$, ascorbic acid, sulphinic acids, sulphites and formamidinesulphinic acids and salts thereof.

Suitable compounds which contain two or more azo units are, for example, reaction products of a) azodicarboxylic acids with compounds which contain more than one oxirane function. Di-, tri- to oligo-compounds and polymers can be obtained in this manner, depending on the oxirane compound used.

A preferred azodicarboxylic acid is, in particular, 4,4'-azobis(4-cyanovaleric acid), which forms suitable free radical initiators, for example, with ethylene glycol diglycidyl ether or with polyglycerol polyglycidyl ethers.

b) Hydroxyl- and amino-functional azo compounds with compounds which contain more than one oxirane or isocyanate group.

Suitable azo compounds are, for example, 2,2'-azo-bis(N,N-dimethyleneisobutyramidine) or the corresponding dihydrochloride, 2,2'-azobis(2-amidinopropane) dihydrochloride, 2,2'-azobis(2-methyl-N-(1,1-bis(hydroxymethyl)-2-hydroxyethyl)propionamide), 2,2'-azobis(2-methyl-N-(1,1-bis(hydroxymethyl)-ethyl)propionamide) or 2,2'-azobis(2-methyl-N-(2-hydroxyethyl)-propionamide), which form suitable free radical initiators, for example with the glycidyl ethers mentioned above under a) or with hexamethylene diisocyanate, tolylene diisocyanate or phenylene diisocyanate.

c) Azobisamides with aldehydes. A suitable azobisamide is, in particular, 2,2'-azobis(isobutyramide) dihydrate, which forms suitable free radical initiators, for example, with formaldehyde or glyoxal.

d) Azobisnitriles with polyalcohols. In particular, reaction products of 2,2'-azobisisobutyronitrile with ethylene glycol, butane-1,4-diol or hexane-1,6-diol are preferred (Makromol. Chem. 178 2533 (1977)).

Suitable initiators are, in addition, polyfunctional photoinitiators, compounds obtained by reaction of $Ce^{4+}$ with polyfunctional alcohols, such as polyvinyl alcohol or cellulose (J. Po. Sci. Volume XXXI, page 242 et seq. (1958)) and ozonized starch (Chemistry and Engineering News, 37 27, 41 (1959)).

The free radical initiators mentioned can be used by themselves or as any desired mixtures with one another for the preparation of the hydrophilic polymers according to the invention.

They are preferably employed here in amounts of 0.001 to 20% by weight, based on the total monomers. 0.05 to 3.0% by weight is particularly preferred.

In a particular embodiment of the present invention, free radical initiators in which the functions which form free radicals have different reactivities or are activated by different mechanisms are used. Such initiators thus contain, for example, both azo and peroxide or hydroperoxide functions, which are activated in succession in a predetermined manner and can thus be used, for example, for the preparation of block polymers.

It may furthermore be of advantage to use initiators in which the functions which form free radicals lie at different spatial distances from one another in the molecule.

The molecular weight of the initiators which can be used for the preparation of hydrophilic polymers according to the invention can of course vary within wide limits. The molecular weights are, in particular, in the range from 100 to 10,000,000.

The hydrophilic polymers according to the invention can also be prepared using suitable crosslinking agents, i.e. compounds having at least two double bonds, which can be polymerized into the polymer network.

The use of crosslinking agents is particularly preferred if the free radical initiators used form only two free radical sites per molecule and therefore do not themselves have crosslinking properties.

On the other hand, free radical initiators which form three or more free radical sites per molecule themselves have crosslinking properties, so that in these cases the crosslinking agents mentioned can also be dispensed with. Nevertheless, the crosslinking agents mentioned can also be used in combination with initiators which form three or more free radical sites per molecule.

Suitable crosslinking agents are, in particular, methylenebisacrylamide and -methacrylamide, esters of unsaturated mono- or polycarboxylic acids with polyols, such as diacrylate or triacrylate, for example butanediol diacrylate or dimethacrylate or ethylene glycol diacrylate or dimethacrylate, trimethylolpropane triacrylate and vinyl methacrylate, and allyl compounds, such as allyl (meth-)acrylate, triallyl cyanurate, diallyl maleate, polyallyl esters, tetraallyloxyethane, triallylamine, tetraallylethylenediamine, allyl esters of phosphoric acid and vinylphosphonic acid derivatives, such as are described, for example, in EP-A 343 427. The content of EP-A 343 427 is also expressly a constituent of the present disclosure.

The crosslinking content is preferably 0 to 20% by weight, particularly preferably 0 to 3% by weight, based on the total monomer content.

Furthermore, the hydrophilic polymers according to the invention can be post-crosslinked in the aqueous gel phase in a manner known per se or crosslinked on the surface in the form of ground and sieved polymer particles. Crosslinking agents which are suitable for this are compounds which contain at least two groups which can form covalent bonds with the carboxyl groups of the hydrophilic polymer. Suitable compounds are, for example, di- or polyglycidyl compounds, such as phosphonic acid diglycidyl ester, alkoxysilyl compounds, polyaziridines, polyamines or polyamidoamines, it also being possible for the compounds mentioned to be used as mixtures with one another (see, for example, EP-A 83 022, EP-A 543 303 and EP-A 530 438). Polyamidoamines which are suitable crosslinking agents are described, in particular, in EP-A 349 935. The content of the abovementioned patent applications is expressly also a constituent of the present disclosure.

The hydrophilic polymers according to the invention can be prepared by known polymerization processes. Polymerization in aqueous solution by the process of so-called gel polymerization is preferred. In this process, 15 to 50% strength by weight aqueous solutions of one or more hydrophilic monomers and, if appropriate, a suitable grafting base are polymerized in the presence of a free radical initiator which can form di- or poly-radicals, preferably without mechanical mixing and utilizing the Trommsdorff-Norrish effect (Bios Final Rep. 363.22; Makromol. Chem. 1, 169 (1947)).

The polymerization reaction can be carried out in the temperature range between 0° C. and 130° C., preferably between 10° C. and 100° C., either under normal pressure or under increased pressure. As is customary, the polymerization can also be carried out in an inert gas atmosphere, preferably under nitrogen.

The quality properties of the polymers can be improved further by subsequently heating the aqueous polymer gels in the temperature range from 50° to 130° C., preferably 70° to 100° C., for several hours, preferably 8 to 15 hours.

The hydrophilic polymers according to the invention prepared by this route, which are in the form of aqueous gels, can be obtained and employed in solid form by known drying processes, after mechanical comminution with suitable apparatuses.

The hydrophilic polymers according to the invention have considerably higher molecular weights than the known polymers of the prior art and have significant advantages compared with these. In particular, they have a high liquid-bonding capacity coupled with simultaneously high liquid retention values and a high mechanical strength of the swollen gel particles, with low extractable contents.

They are therefore outstandingly suitable as absorbents for water and aqueous liquids, such as urine or blood, in hygiene articles such as nappies for babies and adults, bandages, tampons and the like. However, they can also be used as soil-improving agents in agriculture and horticulture, as moisture-binding agents in cable sheathing and for thickening aqueous waste products.

EXAMPLE 1

1.0 g (0.003571 mol) of 4,4'-azobis(4-cyanovaletic acid) was dissolved in 100 g of dimineralized water at 50° C., 0.337 g (0.0019379 mol) of ethylene glycol diglycidyl ether was added and the mixture was left to stand at room temperature for 24 hours. 400 g of dimineralized water were initially introduced into a 1 l glass polymerization flask, 70 g (0.83 mol) of Na bicarbonate were suspended therein, and 200 g (2.77 mol) of acrylic acid were added dropwise such that foaming over was avoided. The monomer solution thereby cooled to about 10° C. The previously prepared initiator solution was then transferred quantitatively to the reaction flask with the aid of 50 ml of dimineralized water as a rinsing agent, and the components were stirred homogeneously. The clear monomer solution was then left to stand under a $CO_2$ atmosphere at room temperature for 14 hours, without stirring and without a reaction being detectable. It was then diluted with 150 ml of dimineralized water, rendered inert by passing in $N_2$ and heated to an internal temperature of 50° C. When this temperature was reached, the polymerization reaction started immediately and a high-viscosity paste was formed, which was after-heated at 50° C. for 12 hours. A 0.1% strength solution of the polymer in demineralized water (based on acrylic acid) had a relative vis-cosity of 28.7335, measured in an Ubbelohde capillary viscometer type Ic at 25° C.

For comparison, the process was repeated, but no ethylene glycol diglycidyl ether was added to the initiator solution. A polymer of which a 0.1% strength solution in demineralized water (based on acrylic acid) had a relative viscosity of 4.3345, measured in an Ubbelohde capillary viscometer type Ic at 25° C., was obtained.

A significantly high molecular weight polymer, expressed by the relative viscosity, was thus obtained by using the initiator which forms di-radicals than by using the initiator which forms mono-radicals.

The resulting gel according to the invention and the comparison gel were kneaded with in each case 44.3% by weight of 50% strength NaOH (based on the acrylic acid) in a kneader until homogeneous, in each case 0.5% by weight (based on the acrylic acid) of methylphosphonic acid diglycidyl ester was then added, the mixture was homogenized at temperatures of 70° to 80° C. and the composition, which was comminuted mechanically after discharge from the kneader, was dried in a stream of air at 180° C. The product was ground and sieved (850/100 μm). The following performance data were obtained:

|  | Extractables | | CRC [g/g] | FSC [g/g] | AUL [g/g |
|---|---|---|---|---|---|
|  | 1 h [%] | 16 h [%] | | | |
| Gel according to the invention | 4.6 | 9.9 | 39 | 58 | 10.6 |
| Comparison | 7.3 | 16.2 | 34 | 54 | 8.2 |

CRC = Centrifuge Retention Capacity
PSC = Free Swell Capacity
AUL = Absorption Under Load [20 g/cm$^2$]

EXAMPLE 2

1 g (0.003571 mol) of 4,4'-azobis-4-cyanovaleric acid was dissolved in 20 ml of dimethylformamide, 0.31 g (0.00178 mol) of ethylene glycol diglycidyl ether was added and the mixture was heated to 50° C. and kept at 50° C. for 14 hours.

600 g of demineralized water were initially introduced into a 1 l polymerization flask, 200 g of acrylic acid were dissolved therein and this solution was heated to an internal temperature of 50° C. while passing in $N_2$. The previously prepared initiator solution, warmed to 50° C. was then transferred quantitatively into the reaction flask. After homogenization, the introduction of $N_2$ was stopped and the reaction solution was left to stand, without stirring. The polymerization reaction started immediately thereafter, a high-viscosity paste being formed. The mixture was after-heated at 50° C. for 12 hours. A 0.1% strength solution of the polymer in demineralized water (based on acrylic acid) had a relative viscosity of 2.5902, measured in an Ubbelohde capillary viscometer type Ic at 25° C.

For comparison, the process was repeated, but no ethylene glycol diglycidyl ether was added to the initiator solution. A polymer whose 0.1% strength solution in demineralized water (based on the acrylic acid) had a relative viscosity of 2.2894, measured in an Ubbelohde capillary viscometer type Ic at 25° C., was obtained.

The product according to the invention and the comparison product were subjected to post-crosslinking as described in Example 1. The following performance data were obtained:

|  | Extractables | | CRC [g/g] | FSC [g/g] | AUL [g/g |
|---|---|---|---|---|---|
|  | 1 h [%] | 16 h [%] | | | |
| Product according to the invention | 5.8 | 10.6 | 36 | 57 | 10.3 |
| Comparison | 8.1 | 16.9 | 33 | 54 | 8.3 |

EXAMPLE 3

Example 2 was repeated, but only 0.155 g (0.00089 mol) of ethylene glycol diglycidyl ether was employed. A polymer of which a 0.1% strength solution in demineralized water (based on the acrylic acid) had a relative viscosity of 4.2890, measured in an Ubbelohde capillary viscometer type Ic at 25° C., was obtained.

The product was subjected to post-crosslinking as described in Example 1. The following performance data were obtained:

| Extractables | | CRC | FSC | AUL |
|---|---|---|---|---|
| 1 h [%] | 16 h [%] | [g/g] | [g/g] | [g/g] |
| 5.7 | 10.3 | 35 | 58 | 9.6 |

EXAMPLE 4

134.5 g of 50% strength NaOH (degree of neutralization= 55 mol %) were stirred slowly into a mixture of 344 g of demineralized water, 300 g of ice from demineralized water and 220 g of acrylic acid in a well-insulated polymerization flask while stirring and under adiabatic conditions. 1 g (0.45% by weight) of methylenebisacrylamide was added, nitrogen was passed into the solution, while stirring, and the mixture was brought to 5° C. 0.19 g of 2,5-dimethylhexane 2,5-dihydroperoxide (product of PEROXID-CHEMIE GmbH, Germany) and then 0.55 g of a 1% strength aqueous ascorbic acid solution were added, the mixture was stirred homogeneously, the stirrer was removed and the mixture was left to stand while passing in further $N_2$. The reaction started after only a few minutes, and in the course thereof the temperature rose to a maximum of about 55° C. and a sliceable gel was formed. This was left to stand under the same conditions for about 6 hours and then comminuted mechanically, dried in a thin layer in a stream of air at 180° C., ground and, if appropriate, sieved. A product was obtained which gave the performance data shown in Table 1.

For comparison, the abovementioned synthesis was repeated, with the difference that instead of 2,5-dimethylhexane 2,5-dihydroperoxide, ammonium peroxodisulphate was employed. The performance data are likewise shown in Table 1.

EXAMPLE 5

Example 4, including the comparison, was repeated, but instead of 0.45% by weight, 0.87% by weight of methylenebisacrylamide was employed. The performance data can be seen from Table 1.

EXAMPLE 6

Example 4, including the comparison, was repeated, but instead of 0.45% by weight, 1.36% by weight of methylenebisacrylamide was employed. The performance data are to be found in Table 1.

EXAMPLE 7

The following were employed in accordance with Example 4:

220 g of acrylic acid neutralized with $NaHCO_3$ to a degree of neutralization of 55 mol %.

0.3% by weight, based on the acrylic acid, of trimethylolpropane triacrylate as the crosslinking agent. 0.068% by weight, based on the acrylic acid, of the reaction product of 2,2'-azobisisobutyronitrile with butane-1,4-diol (Pinner synthesis analogously to Example 1b from Makromol. Chem. 178, 2533 (1977)) as the free radical initiator.

For comparison, the synthesis was repeated, but instead of the abovementioned free radical initiator, only the starting substances for its preparation were added. The performance data are to be found in Table 1.

EXAMPLE 8 a) Preparation of the free radical initiator:

288 g (1 mol) of 2,2'-azobis-2-methyl-N-(2-hydroxyethyl)-propionamide were introduced slowly into a solution of 600 ml of anhydrous cyclohexane and 140 g (1 mol) of hexamethylene diisocyanate and 0.3 g of dibutyltin dilaurate, as the catalyst, while stirring, the reaction temperature being kept constant at 0° to 10° C. by external cooling. The mixture was subsequently stirred at room temperature for 30 to 60 minutes, and the precipitate formed was then filtered off and freed from residual solvent under reduced pressure at a maximum of 40° C.

b) Preparation of the polymer according to the invention:

The following were reacted in accordance with Example 4:

220 g of a mixture of acrylic acid and vinylphosphonic acid in a molar ratio of 100:1, neutralized with $NarCO_3$ to a degree of neutralization of 55 mol %.

0.3% by weight, based on the monomers, of trimethylolpropanetriacrylate as the crosslinking agent.

0.068% by weight, based on the monomers, of the initiator prepared in accordance with a).

For comparison, the synthesis was repeated, but instead of the abovementioned free radical initiator, only the starting substances for its preparation were added. The performance data are to be found in Table 1.

EXAMPLE 9 a) Preparation of the Free Radical Initiator

A solution (slightly cloudy) of 23.6 g (0.1 mol) of 2,2'-azobis(2-methylpropionamide) dihydrate in 500 g of water was brought to a weakly basic pH of 7.5 with dilute sodium carbonate solution. 14.5 g (0.1 mol) of 40% strength aqueous glyoxal were then added and the reaction solution was heated to 40° C. and stirred at this temperature for 6 hours. After being cooled to <20° C., the reaction solution was employed directly for the polymerization experiments.

b) Preparation of the Polymer According to the Invention

The following were reacted in accordance with Example 4:

220 g of acrylic acid which, after the polymerization, was neutralized with NaOH to a degree of neutralization of 70 mol %.

0.45% by weight, based on the acrylic acid, of tetraallyloxyethane as the crosslinking agent.

0.091% by weight, based on the acrylic acid, of the initiator prepared in accordance with a).

For comparison, the synthesis was repeated, but instead of the abovementioned free radical initiator, only the starting substances for its preparation were added. The performance data are to be found in Table 1.

EXAMPLE 10

The following were reacted in accordance with Example 4:

632 g of 2-acrylamido-2-methylpropanesulphonic acid, neutralized with $NaHCO_3$ to a degree of neutralization of 70 mol %.

0.1% by weight, based on the monomer, of tetraallyloxyethane as the crosslinking agent.

0.046% by weight, based on the monomer, of the initiator prepared according to Example 9a).

For comparison, the synthesis was repeated, but instead of the abovementioned initiator, only the starting substances for its preparation were added. The performance data are to be found in Table 1.

EXAMPLE 11

The following were reacted in accordance with Example 4:

220 g of acrylic acid, neutralized with NaHCO$_3$ to a degree of neutralization of 55 mol %.

0.3% by weight, based on the acrylic acid, of trimethylolpropane triacrylate.

0.022% by weight, based on the acrylic acid, of 2,5-dimethylhexane 2,5-dihydroperoxide and 0.025% by weight, based on the acrylic acid, of the free radical initiator employed in Example 7.

For comparison, the synthesis was repeated, but instead of the abovementioned initiator mixture, only a mixture of 2,2'-azobisisobutyronitrile and butane-1,4-diol was added. The performance data are to be found in Table 1.

EXAMPLE 12 a) Preparation of the Free Radical Initiator

Apparatus: double-walled glass beaker electrolysis cell having a ground glass adaptor on the side, Teflon stopper with bores for electrodes, gas inlet tube and thermometer; Pt sheet electrodes on holder; cryostat; galvanostat with current leads, measuring equipment and the like.

0.35 g of NaOH (0.0086 mol) was added to 150 g of an aqueous solution which contained 8.3% (12.45 g, 0.173 molar equivalent of COOH) of polyacrylic acid ($M_w$=about 200,000), and the mixture was transferred to the electrolysis cell and temperature-controlled at 10° C. with the aid of a cryostat. A constant stream of O$_2$ was now passed into the solution via the gas inlet tube, onto the lower end of which was fused a glass frit. Electrolysis was carried out under a current of 150 mA, while stirring, up to a charge throughput of 1800 C, the internal temperature being kept at 10° C. and the electrolyte being flushed constantly with oxygen. The electrolysate was employed in this form directly for the polymerization experiments.

b) Preparation of the Polymer According to the Invention

The following were reacted in accordance with Example 4:

220 g of acrylic acid which, after the polymerization, was neutralized with NaOH to a degree of neutralization of 68 mol %.

5.8% by weight, based on the acrylic acid, of the initiator prepared according to a).

The performance data are to be found in Table 1.

For comparison, the synthesis was repeated, the solution mentioned under a) being employed as the initiator without electrolysis. No polymerization took place under these conditions (Comparison 1).

The comparison was repeated, but 0.09% by weight, based on the acrylic acid, of ammonium peroxodisulphate additionally being added. A water-soluble, non-swellable polymer was formed under these conditions (Comparison 2).

EXAMPLE 13

The synthesis according to Example 12 was repeated, 0.1% by weight, based on the acrylic acid, of methylenebisacrylamide additionally being added.

For comparison, the synthesis was repeated, but the solution mentioned under a), without electrolysis, and 0.09% by weight, based on the acrylic acid, of ammonium peroxodisulphate were employed as the initiator. The performance data are to be found in Table 1.

TABLE 1

Performance data of the polymers according to Examples 4 to 13.

| | Extractables | | | | |
|---|---|---|---|---|---|
| Example | 1 h [%] | 16 h [%] | CRC [g/g] | PSC [g/g] | AUL [g/g] |
| 4 | 4.3 | 7.4 | 38 | 54 | 9.4 |
| 4 Comparison | 8.1 | 19.2 | 35 | 52 | 9 |
| 5 | 1.9 | 4.5 | 28 | 47 | 21.4 |
| 5 Comparison | 6.6 | 9.1 | 29 | 45 | 15.4 |
| 6 | 1 | 2.9 | 22 | 40 | 25.3 |
| 6 Comparison | 4.3 | 7.5 | 21 | 39 | 20.9 |
| 7 | 5.1 | 8.2 | 43 | 63 | 9 |
| 7 Comparison | 9.9 | 20 | 39 | 60 | 8.1 |
| 8 | 8.1 | 12.4 | 35 | 70 | 8.6 |
| 8 Comparison | 12 | 19.3 | 29 | 63 | 8.4 |
| 9 | 6.3 | 8.1 | 31 | 55 | 11.4 |
| 9 Comparison | 7.5 | 9.7 | 26 | 49 | 9.9 |
| 10 | 9.9 | 13.1 | 31 | 54 | 8.4 |
| 10 Comparison | 11.2 | 16.2 | 27 | 50 | 8.1 |
| 11 | 4.5 | 8.2 | 44 | 58 | 10 |
| 11 Comparison | 6.2 | 9.1 | 39 | 51 | 8.8 |
| 12 | 7.6 | 16.3 | 26 | 58 | 8.3 |
| 12 Comparison 1 | no polymerization | | | | |
| 12 Comparison 2 | water-soluble polymer | | | | |
| 13 | 5.6 | 14.4 | 28 | 57 | 9.7 |
| 13 Comparison | 7.3 | 16.9 | 25 | 56 | 8.1 |

We claim:

1. Water-swellable hydrophilic polymers which comprise polymers prepared by free radical (co)polymerization of one or more hydrophilic monomers of the formula I

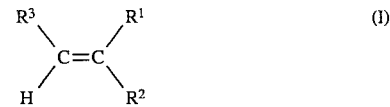  (I)

wherein

R$^1$ is hydrogen, methyl or ethyl,

R$^2$ is the group —COOR$^4$, the eulphonyl group, the phosphonyl group, the phosphonyl group esterified by (C$_1$–C$_4$)-alkanol or a group of the formula

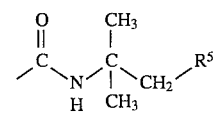

R$^3$ is hydrogen, methyl, ethyl or the carboxyl group,

R$^4$ is hydrogen, amine or hydroxy-(C$_1$–C$_4$)-alkyl and

R$^5$ is the sulphonyl group, the phosphonyl group or the carboxyl group, or grafting (co)polymerization of one or more hydrophilic monomers of the formula I onto a grafting base, using a free radical initiator which forms three or more free radical sites per molecule, and wherein crosslinking is accomplished in the absence of a crosslinking agent.

2. Water-swellable hydrophilic polymers which comprise polymers prepared by free radical (co)polymerization of one or more hydrophilic monomers of the formula I

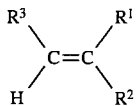   (I)

wherein $R^x$ is hydrogen, methyl or ethyl, $R^2$ is the group —COOR$^4$, the sulphonyl group, the phosphonyl group, the phosphonyl group esterified by $(C_1-C_4)$-alkanol or a group of the formula

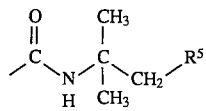

$R^3$ is hydrogen, methyl, ethyl or the carboxyl group, $R^4$ is hydrogen, amino or hydroxy-$(C_1-C_4)$-alkyl and $R^5$ is the sulphonyl group, the phosphonyl group or the carboxyl group, using a free radical initiator obtained by anodic oxidation of a polycarboxylic acid and wherein crosslinking is performed in the absence of a crosslinking agent.

3. Water-swellable hydrophilic polymers according to claim 1, wherein said free radical initiator is obtained by anodic oxidation of polycarboxylic acids in the presence of oxygen.

4. The water-swellable hydrophilic polymers according to claim 2, further comprising a crosslinking agent and the resultant polymer would be water-swellable even if the crosslinking agent had not been added.

5. The water-swellable hydrophilic polymers according to claim 1, wherein said hydrophilic monomers are selected from the group consisting of acrylic acid, methacrylic acid, vinylsulphonic acid, vinylphosphonic acid, maleic acid, fumaric acid, itaconic acid, 2-acrylamido-2-methylpropane-sulphonic acid and their amides, hydroxyalkyl esters, esters containing amino groups, amides containing amino groups and ammonium groups.

6. The water-swellable hydrophilic polymers according to claim 1, wherein said hydrophilic monomers are acrylic acid or methacrylic acid.

7. The water-swellable hydrophilic polymers according to claim 1, further comprising a crosslinking agent and the resultant polymer would be water-swellable even if the crosslinking agent had not been added.

8. The water-swellable hydrophilic polymers according to claim 1, wherein said grafting base is starch, cellulose, polysaccharide, oligosaccharide, polyalkaline oxide or hydrophilic polyesters.

9. Water-swellable hydrophilic polymers according to claim 1, wherein said grafting base is starch, polyethylene-oxide or polypropylene-oxide.

10. Water-swellable hydrophilic polymers according to claim 1, wherein said free radical initiator is a compound which contains at least three hydroperoxide units, peroxide units or azo units.

11. Water-swellable hydrophilic polymers according to claim 1, wherein said free radical initiator is a reaction product of 4,4'-azobis (4-cyanovaleric acid) with a polyglycerol polyglycidyl ether.

12. The water-swellable hydrophilic polymers according to claim 1, wherein said free radical initiator's are present in amount from about 0.001 to about 20% by weight based on the total monomers.

13. The water-swellable hydrophilic polymers according to claim 1, wherein said free radical initiator's are present in amount from about 0.05 to about 3% by weight based on the total monomers.

14. Water-swellable hydrophilic polymers according to claim 1, further comprising a crosslinking agent.

15. The water-swellable hydrophilic polymers according to claim 14, wherein said crosslinking agent is selected from the group consisting of methylenebisacrylamide, methylenebismethacrylamide, esters of unsaturated mono- or polycarboxylic acids with polyols, allyl (meth)acrylate, triallyl cyanurate, diallyl maleate, polyallyl esters, tetraallyloxyethane, triallylamine, tetraallylsthylenediamine, allyl esters of phosphoric acid and vinylphosphonic acid derivatives.

16. The water-swellable hydrophilic polymers according to claim 15, wherein said crosslinking agent is present is an effective amount to provide crosslinking properties up to about 20% by weight based on the total monomer content.

17. The water-swellable hydrophilic polymers according to claim 15, wherein said crosslinking agent is present is an effective amount to provide crosslinking properties up to about 3% by weight based on the total monomer content.

18. An absorbent comprising the water-swellable hydrophilic polymer according to claim 1.

19. Hygiene articles comprising said absorbent as claimed in claim 18, mixed with water or aqueous liquids.

* * * * *